US00PP36184P2

(12) United States Plant Patent
Heuger

(10) Patent No.: US PP36,184 P2
(45) Date of Patent: Oct. 1, 2024

(54) ***HELLEBORUS* PLANT NAMED 'HL 1016'**

(50) Latin Name: ***Helleborus niger* x *Helleborus* x *hybridus***
Varietal Denomination: HL 1016

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/518,338

(22) Filed: Nov. 22, 2023

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Helleborus* plant named 'HL 1016' characterized by its upright to somewhat outwardly spreading and mounded plant habit; moderately vigorous growth habit; dark green-colored leaflets with lighter green-colored venation; freely flowering habit; double-type light purple-colored flowers; and good garden performance.

2 Drawing Sheets

Figure 1:
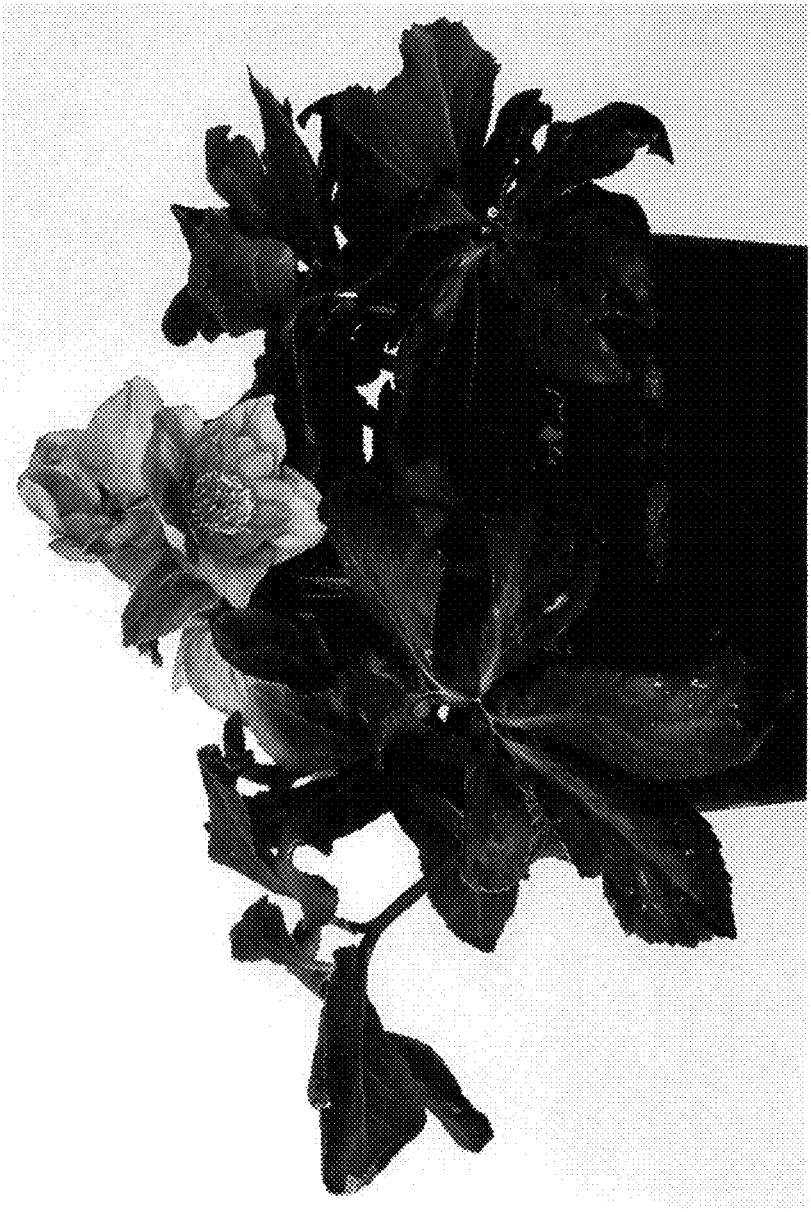

Botanical designation: *Helleborus niger* x *Helleborus* x *hybridus*.

Cultivar denomination: 'HL 1016'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 20, 2023, application No. 2023/1372. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus niger* X *Helleborus* x *hybridus* and hereinafter referred to by the name 'HL 1016'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in November, 2012 of a proprietary selection of *Helleborus niger* identified as code No. P571, not patented, as the female, or seed, parent and a proprietary selection of *Helleborus* x *hybridus* identified as code No. O1512, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2014.

Asexual reproduction of the new *Helleborus* plant by in vitro axillary meristem culture in a controlled environment in Glandorf, Germany since April, 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1016'. These characteristics in combination distinguish 'HL 1016' as a new and distinct *Helleborus* plant:

1. Upright to somewhat outwardly spreading and mounded plant habit.
2. Moderately vigorous growth habit.
3. Dark green-colored leaflets with lighter green-colored venation.
4. Freely flowering habit.
5. Double-type light purple-colored flowers.
6. Good garden performance.

Plants of the new *Helleborus* differ from plants of the female parent selection in the following characteristics:

1. Plants of the new *Helleborus* have double-type flowers whereas plants of the female parent selection have single-type flowers.

2. Flowers of plants of the new *Helleborus* are darker purple in color than flowers of plants of the female parent selection.

Plants of the new *Helleborus* differ from plants of the male parent selection in the following characteristics:

1. Leaflets of plants of the new *Helleborus* are darker green in color than leaflets of plants of the male parent selection.
2. Flowers of plants of the new *Helleborus* are lighter purple in color than flowers of plants of the male parent selection.

Plants of the new *Helleborus* can also be compared to plants of *Helleborus niger* 'COSEH210', disclosed in U.S. Plant Pat. No. 21,048. In side-by-side comparisons, plants of the new *Helleborus* differ primarily from plants of 'COSEH210' in the following characteristics:

1. Plants of the new *Helleborus* have double-type flowers whereas plants of 'COSEH210' have single-type flowers.
2. Plants of the new *Helleborus* have light purple-colored flowers whereas plants of 'COSEH210' have white-colored flowers.

BRIEF DESCRIPTION OF THE PHOTOGRAPHS

Figure 2:
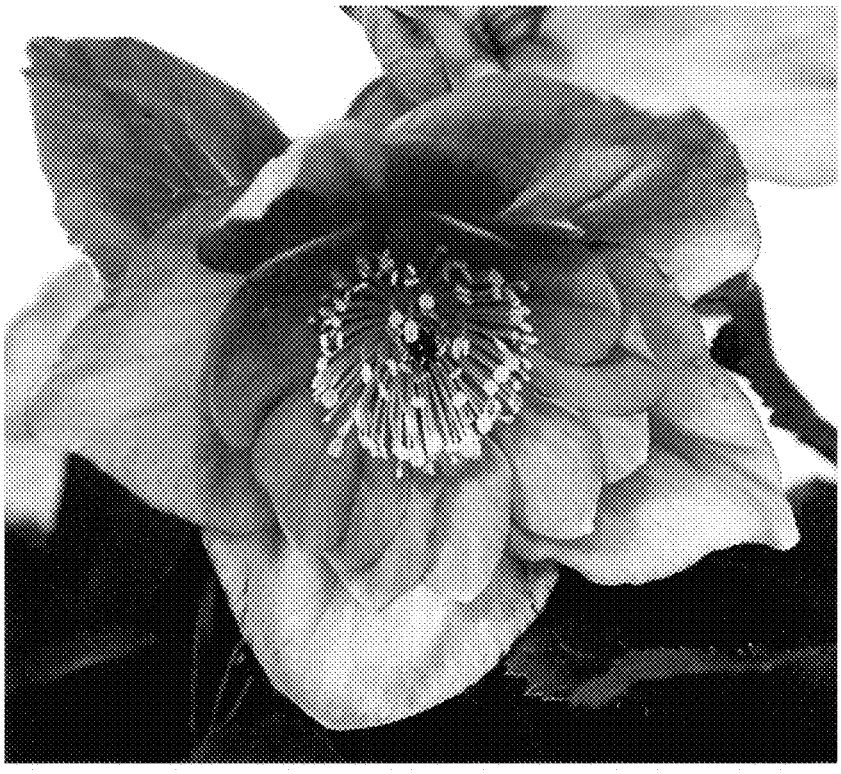

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant. The photograph on the first sheet (FIG. 1) is a side perspective view of a typical flowering plant of 'HL 1016' grown in a container. The photograph on the second sheet (FIG. 2) is a close-up view of a typical flower of 'HL 1016'.

DETAILED BOTANICAL DESCRIPTION

The aforementioned photographs and following observations, measurements and values describe plants grown during the winter in 29-cm containers in a glass-covered greenhouse in Glandorf, Germany and under cultural practices typical of commercial *Helleborus* production. During the production of the plants, day temperatures ranged from 12C to 32C and night temperatures ranged from 5C to 12C. Plants were 48 weeks old when the photographs were taken and 16 months old when the description was taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'HL 1016'.

Parentage:

*Female, or seed, parent*.—Proprietary selection of *Helleborus niger* identified as code No. P571, not patented.

*Male, or pollen, parent*.—Proprietary selection of *Helleborus x hybridus* identified as code No. O1512, not patented.

Propagation:

*Type*.—In vitro axillary meristem culture.

*Time to initiate roots, winter*.—About 55 days at temperatures about 12C.

*Time to produce a rooted young plant, winter*.—About 170 days at temperatures ranging from about 4C to 15C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held above the foliar plane; plant shape, roughly flattened globular; moderately vigorous growth habit and moderate growth rate.

*Plant height, soil level to top of foliar plane*.—About 16.8 cm.

*Plant height, soil level to top of flowers*.—About 25.4 cm.

*Plant diameter* (*area of spread*).—About 47.3 cm.

Leaf description:

*Arrangement*.—Leaves arranged in a basal rosette; leaves palmately compound with typically five, or occasionally, seven, leaflets per leaf.

*Leaf length*.—About 20.6 cm.

*Leaf width*.—About 23.4 cm.

*Leaflet length*.—About 12 cm.

*Leaflet width*.—About 6.9 cm.

*Leaf shape*.—Palmate; roughly reniform in outline.

*Leaflet shape*.—Elliptic to close to obovate.

*Leaflet apex*.—Acute.

*Leaflet base*.—Attenuate.

*Leaflet margin*.—Serrate; slightly coarsely undulate.

*Leaflet texture and luster, upper surface*.—Smooth, glabrous; coriaceous and tough; moderately glossy.

*Leaflet texture and luster, lower surface*.—Smooth, glabrous; coriaceous and tough; slightly glossy.

*Leaflet venation pattern*.—Pinnate and reticulate.

*Leaflet color*.—Developing leaflets, upper surface: Close to 143A; at the base, strongly tinged with close to 187A. Developing leaflets, lower surface: Close to 146D; midvein, strongly tinged with close to 187A.. Fully developed leaflets, upper surface: Darker than 147A; at the base, tinged with close to 200A and 200B; venation, close to 144A and 144B. Fully developed leaflets, lower surface: Close to 147B; venation, close to 145B.

*Petioles*.—Length: About 15 cm. Diameter: About 7 mm by 7.5 mm. Strength: Strong. Texture and luster, upper and lower surfaces: Smooth, glabrous; slightly glossy. Color, upper surface: Close to 146C; heavily covered with fine dots, close to N199B or 200A. Color, lower surface: Close to 144A to 144B; moderately to heavily covered with fine dots, close to N199A or N186C.

Flower description:

*Flower shape and habit*.—Double-type rotate bowl-shaped flowers arranged in panicles; freely flowering habit with about three flowers per inflorescence and about 30 flowers and flower buds per plant; flowers face mostly outwardly to slightly nodding.

*Fragrance*.—None detected.

*Natural flowering season*.—Plants begin flowering about ten months after planting; plants flower naturally from late autumn into the winter in Germany.

*Flower longevity on the plant*.—About ten days; sepals persistent, other flower parts are not persistent.

*Flower buds*.—Length: About 2.6 cm. Diameter: About 1.4 cm. Shape: Ovate. Texture and luster: Smooth, glabrous; matte. Color: Close to 186B to 186C; towards the base, close to 145D; venation, close to 60B.

*Inflorescence height* (*including peduncle*).—About 24.3 cm.

*Inflorescence diameter*.—About 12.4 cm.

*Flower diameter*.—About 9.7 cm.

*Flower depth*.—About 3.5 cm.

*Petals*.—Petals are not transformed into nectaries. Quantity and arrangement: About 13 to 19, arranged in one or two whorls. Length: About 3.7 cm. Width: About 1.8 cm. Shape: Elliptic to obovate; slightly concave. Apex: Acute. Base: Attenuate. Margin: Entire; not undulate. Texture and luster, upper surface: Smooth, glabrous; slightly velvety; matte. Texture and luster, lower surface: Smooth, glabrous; matte. Color: When opening, upper surface: Close to a blend of N74D and N75A; towards the apex, close to N75B. When opening, lower surface: Close to NN74C. Fully opened, upper surface: Close to 75A; venation, close to 75A; with subsequent development, color becoming closer to 75C and towards the apex, closer to 145C. Fully opened, lower surface: Close to 75A; venation, close to 72B; with subsequent development, color becoming closer to 75C, towards the apex, closer to 145C and venation, close to 71B.

*Sepals*.—Quantity and arrangement: About five, arranged in a single whorl. Length: About 5.3 cm. Width: About 4.9 cm. Shape: Broadly ovate; slightly concave. Apex: Acute to obtuse. Base: Cuneate. Margin: Entire; slightly coarsely undulate. Texture and luster, upper surface: Smooth, glabrous; matte. Texture and luster, lower surface: Smooth, glabrous; matte to slightly glossy. Color: When opening, upper surface: Close to 70B; towards the apex, close to 76C. When opening, lower surface: Close to 70B; towards the apex, close to 75A to 75C; venation, close to 71B and 71C. Fully opened, upper surface: Close to 75A; towards the center, close to 75D; towards the apex, tinged with close to 145C; venation, similar to lamina colors; with subsequent development, color becoming closer to 145B. Fully opened, lower surface: Close to 70A to 70C; towards the center, close to 75D; towards the apex, tinged with close to 145C; venation, similar to lamina colors; with subsequent development, color becoming closer to 145B and venation, close to 71B.

*Flower bracts*.—Quantity per flower: Typically one or two. Length: About 7.1 cm. Width: About 5.1 cm. Shape: Broadly ovate to broadly oblong. Apex: Broadly acute to three-lobed. Base: Cuneate. Margin: Mostly entire; distally, sparsely and shallowly serrate; strongly coarsely undulate. Color, upper surface: Close to 137A; at the base, close to 146D. Color, lower surface: Close to a blend of 138A and 147B; midvein, close to 187A.

*Peduncles*.—Length: About 17.5 cm. Diameter: About 7 mm to 10 mm. Aspect: About 10 degrees from vertical. Strength: Strong. Texture and luster: Smooth, glabrous; moderately glossy. Color: Close to N186C and 187A; heavily covered with fine dots, close to 146D.

*Pedicels*.—Length: About 3.5 cm. Diameter: About 4 mm. Aspect: About 15 degrees from peduncle axis. Strength: Moderately strong. Texture and luster: Smooth, glabrous; moderately glossy. Color: Close to between N186C and 187A; moderately covered with fine dots, close to 146D.

*Reproductive organs*.—Stamens: Quantity per flower: About 100. Filament length: About 1.6 cm. Filament color: Close to 75D. Anther shape: Double and broadly reniform; basifixed. Anther size: About 1.5 mm by 2.5 mm. Anther color: Close to 154D. Pollen amount: Moderate. Pollen color: Close to 4D to lighter than 4D. Pistils: Quantity per flower: About six to eight. Pistil length: About 8 mm. Stigma diameter: About 0.3 mm. Stigma shape: Club-shaped. Stigma color: Close to 156D. Style length: About 0.75 cm. Style color: Close to 187D. Ovary color: Close to 150D; adaxial rib, close to 187D.

Garden performance: Plants of the new *Helleborus* have been observed to have good garden performance and to tolerate rain, wind, high temperatures about 35C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1016' herein as illustrated and described.

* * * * *